United States Patent
Burtscher et al.

(10) Patent No.: US 6,835,064 B2
(45) Date of Patent: Dec. 28, 2004

(54) LIGHT HARDENING DEVICE AND METHOD FOR HARDENING A POLYMERIZABLE MASS FOR DENTAL APPLICATIONS

(75) Inventors: Peter Burtscher, Rankweil (AT); Wolfgang Plank, Rankweil (AT); Gottfried Rohner, Altstatten (CH)

(73) Assignee: Ivoclar Vivadent AG, Schaan (LI)

( * ) Notice: Subject to any disclaimer, the term of this patent is extended or adjusted under 35 U.S.C. 154(b) by 321 days.

(21) Appl. No.: 10/235,872

(22) Filed: Sep. 5, 2002

(65) Prior Publication Data

US 2003/0091955 A1 May 15, 2003

Related U.S. Application Data

(60) Provisional application No. 60/344,139, filed on Dec. 21, 2001.

(30) Foreign Application Priority Data

Nov. 9, 2001 (DE) .......................................... 101 55 034

(51) Int. Cl.$^7$ ............................................... A61C 19/00
(52) U.S. Cl. ......................................... 433/29; 433/229
(58) Field of Search .............................. 433/29; 362/119

(56) References Cited

U.S. PATENT DOCUMENTS 5,420,768 A    5/1995  Kennedy
5,634,711 A    6/1997  Kennedy et al.
6,200,134 B1   3/2001  Kovac et al.
6,318,996 B1   11/2001 Melikechi et al.
6,331,111 B1   12/2001 Cao

FOREIGN PATENT DOCUMENTS

DE   295 11 927 U1    2/1997
DE   196 19 154 A1    6/1997
DE   198 10 573 A1    9/1999
WO   WO 97/36552 A1   10/1997
WO   WO 00/13608 A1   3/2000

*Primary Examiner*—Kevin Shaver
*Assistant Examiner*—Candice C. Stokes
(74) *Attorney, Agent, or Firm*—John C. Thompson; Alan S. Koriuan

(57) ABSTRACT

A light hardening device is provided for hardening a light hardenable mass applied for dental purposes that has a first light emitting diode for emitting light at a range of intensities corresponding to a set of wavelengths which at most only partially overlap a range of light sensitivities of a photo initiator comprised in the mass. The light hardening device also includes a second light emitting diode for emitting light at a range of intensities corresponding to a set of wavelengths which overlap the set of photo initiator light sensitivities to a relatively greater extent than the partial overlap of the range of first light emitting diode intensities with the range of photo initiator light sensitivities.

16 Claims, 2 Drawing Sheets

LIGHT HARDENING DEVICE AND METHOD FOR HARDENING A POLYMERIZABLE MASS FOR DENTAL APPLICATIONS

CROSS-REFERENCE TO RELATED APPLICATIONS

This application claims foreign priority benefits under 35 U.S.C. §119(a)–(d) from German patent application Ser. No. P 101 55 034.0 filed Nov. 9, 2001. In addition, this application claims the benefit under 35 U.S.C. §119(e) of U.S. provisional patent application Ser. No. 60/344,139 filed Dec. 21, 2001.

BACKGROUND OF THE INVENTION

The present invention relates to a light hardening device as well as a method for polymerization of polymerizable masses. Light hardening devices of this type are used, for example, if light polymerizable masses or material are to be hardened in a focused manner.

The polymerizable materials which can be hardened by light hardening devices, as is conventionally known, are, for example, cements, an excess amount of which must be applied to complete the application task. The oversupply or excess amount of cement is extremely hard after the complete hardening of the mass or material, and a high degree of effort is required in order to remove this excess material with suitable dental instruments such as, for example, by milling. Moreover, the removal of hardened excess material causes a high wearing away of the scraping or sharpening instruments or, respectively, the milling instruments.

It has been proposed, for example, to use two photo initiators, which have different spectral sensitivity maximums, and to harden the mass or material completely with lamps or lights having the corresponding emission spectrum.

It has further been proposed in the prior art, with respect to photo polymerizable materials which comprise two different photo initiators, to initially activate the first photo initiator by irradiation thereof by an appropriate wavelength so as to thereby partially harden the material, to thereafter remove the excess material, and subsequently, via a second photo initiator, to undertake the complete hardening of the material. Such systems have, however, not found full acceptance due to the considerable effort required to deploy two photo initiators and the switching over work required to switch between the double systems to effect the partial hardening of the material is difficult to control. Therefore, the excess material is typically removed after the complete hardening of the material which requires, however, a considerable effort.

OBJECTS AND SUMMARY OF THE INVENTION

The present invention offers a solution to the challenge of providing a light hardening apparatus as well as a method for polymerization which permits the realization of an improved material cohesiveness to be achieved by light hardening while nonetheless offering more flexibility to use different polymerizable masses or material.

The light hardening device of the present invention, or, respectively, the inventive method, uses simple means to offer the possibility to completely harden the polymerizable mass or material in a step-wise manner whereby, in the first step, a partially polymerized, easily workable material is created and, in a second step, the finished, completely hardened material is created.

In accordance with the present invention, it is particularly advantageous that a removal of the excess material is possible in spite of the sole use of a single photo initiator to realize a partial polymerization. In this connection, a spectral overlapping between the emission spectrum of a light emitting diode and the sensitivity spectrum of the photo initiator is used to advantage. It is particularly advantageous, in this connection, that one can also work with commercially available, cost favorable dental masses or materials—that is, no special masses or materials requiring two photo initiators need be used. This provides a significant cost advantage alone for the reason that the photo polymerizable masses or material can be polymerized with solely a single photo initiator which can be manufactured in a standardized manner in comparatively large amounts, which leads to significant cost savings with respect to the production and storage of such material. In contrast, special masses are substantially more difficult to work with and more expensive for the reason alone that the storability or shelf life of such special masses is not unlimited.

In contrast, it is particularly advantageous that the light hardening device of the present invention is able to effect polymerization of a photo polymerizable mass or material with solely a single photo initiator. In accordance with the present invention, a system comprising a single light hardening apparatus or device can be used in combination with the photo polymerizable mass or material.

Surprisingly, it has been discovered that the partial overlapping between the emissions spectrum of the first light emitting diode and the sensitivity spectrum of the photo initiator provides the possibility to achieve a partial hardening of the mass or material in a manner such that, during a pause in the hardening process, excess material can be removed while not foreclosing undertaking a further hardening following the pause in the hardening process.

The relationship between the intensities of the light output during the first time period and the light output during the second time period can be accommodated to a wide range of requirements as can the duration of the first and second time periods as well. Advantageously, the emissions intensity of the first light emitting diode is set at at least 100 mW/cm$^2$ while the light intensity of the light emitting diode is set at at least 300 mW/cm$^2$ and is preferably set at 600 to 1,000 mW/cm$^2$. In connection with a high light intensity of the first light emitting diode and/or a relatively long first time period, the partially polymerized material is somewhat firmer so that the removal of excess material can also be undertaken mechanically with commercially available dental instruments while, in connection with a relatively lower light intensity and/or a relatively shorter first time period, a sculpting or, respectively, a working of the mass or material can be undertaken.

It is, in any event, important that the spectrum of the first light emitting diode and the sensitivity of the photo initiator are clearly differentiated from one another and, especially, that the maxima of the two parameters have clearly differentiated wavelengths.

Preferably, the intensity maximum of the first light emitting diode is chosen such that its wavelength is greater than the wavelength of the sensitivity maximum of the photo initiator. For example, camphor quinone can be used as a photo initiator and the first light emitting diode can be configured as a green light emitting diode. The wavelength maxima values are then between around 470 and 505 nanometers; therefore, the wavelength is clearly different than that of the photo initiator.

In accordance with a particularly advantageous configuration of the present invention, the second light emitting diode is chosen such that its emission maximum coincides with the sensitivity maximum of the photo initiator while, at the same time, the spectrums are, to the greatest extent possible, coincidental with one another.

It is to be understood, however, that in lieu of a light emitting diode or a plurality of light emitting diodes, at least one group of LEDs or, respectively, so-called pads, can be deployed. U.S. patent applications 10/139,308, 10/139,308, and 10/177,014 are, in this regard, fully incorporated by reference herein.

BRIEF DESCRIPTION OF THE DRAWINGS

Further advantages, details, and features of the present invention are set forth in the following description of an embodiment of the present invention described in connection with the drawings, in which.

DETAILED DESCRIPTION OF THE PREFERRED EMBODIMENT

Figure 1:
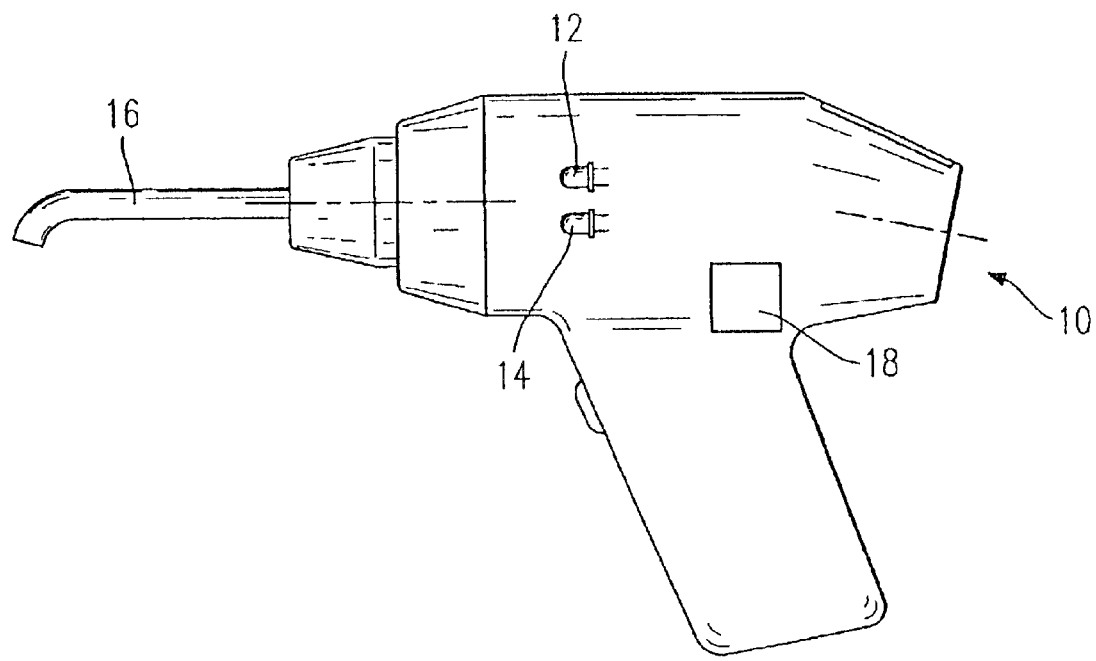
FIG. 1 is a schematic view of an embodiment of a light hardening device of the present invention having two light emitting diodes of differing emission spectrums.

The light hardening device 10 shown in FIG. 1 is configured as a hand operable device that is either connected by a cable (not shown) to a main power supply or is provided with a battery or accumulator for operation independent of a main power supply. The light hardening device includes a blower (not shown) for cooling the light source of the device.

In accordance with the present invention, several light emitting diodes or LEDs are provided, whereby the term "light emitting diodes" includes as well the concept of laser diodes and other fixed body light emitters. In FIG. 1, a first green light emitting diode 12 is illustrated. The light emitting diode 12 is disposed adjacent to a second blue light emitting diode 14 so that light from one or the other of the light emitting diodes can be selectively guided to a light guide 16 for passage therethrough exteriorly of the light hardening device onto the mass in the dental region to be irradiated.

Although only a light emitting diode 12 and a light emitting diode 14 are illustrated, it is to be understood that, in practice, a multiple arrangement of identical light emitting diodes can be used which are commonly actuated and operated as a group.

In accordance with the present invention, it is advantageous if the light emitting diodes 12 and 14 are controlled by a control device 18 which is schematically shown in FIG. 1. The control device permits a program controlled actuation in which the intensity and the time period are pre-programmed but which permits, within certain limits, via programming steps, variation of the program by the user, whereby it is possible to provide an accommodation of the program to the parameters of the dental material which has been applied.

Figure 2:
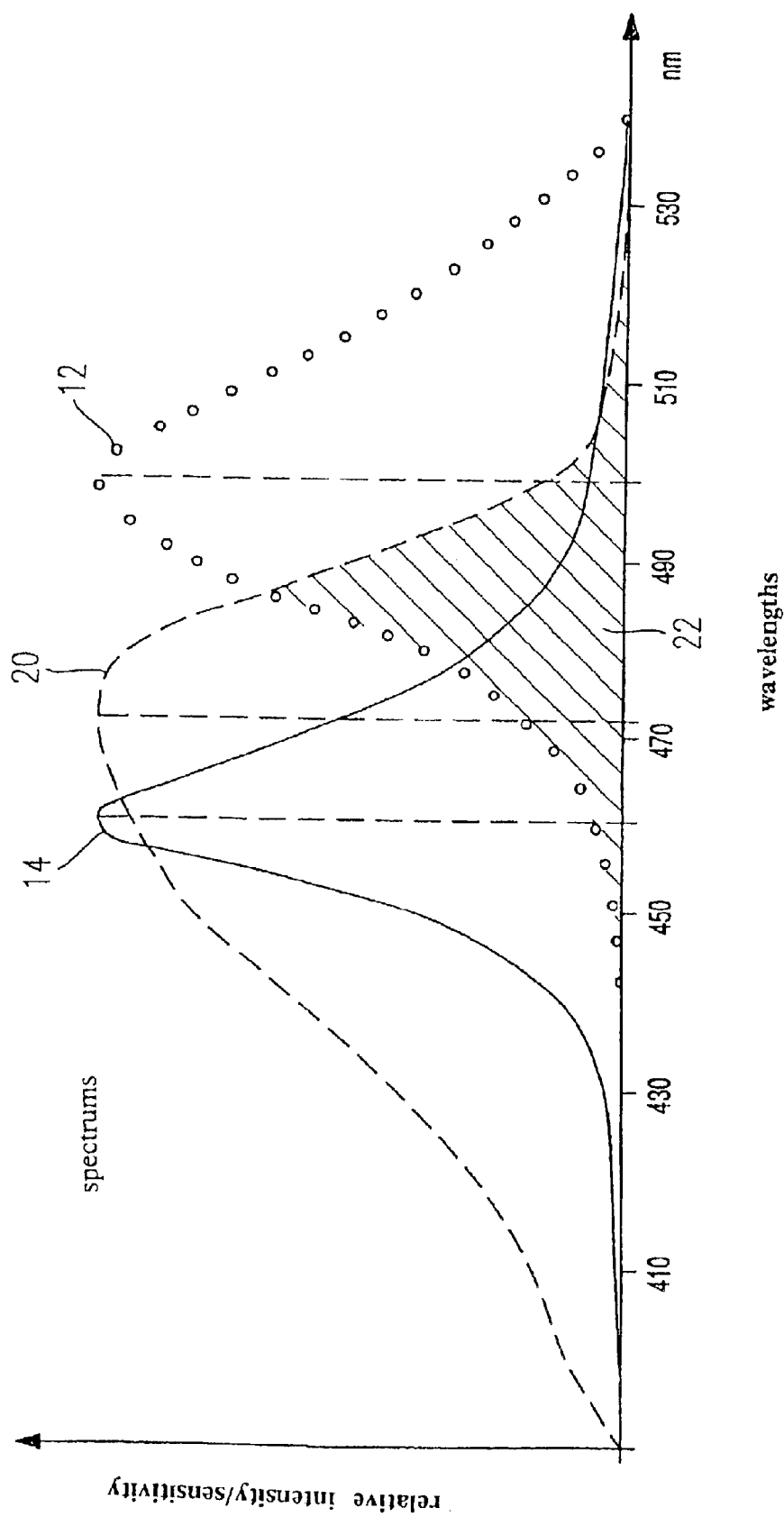
FIG. 2 is a graphical diagram of the emission and sensitivity spectrums of the light hardening device shown in FIG. 1.

In FIG. 2, a diagram of the emission spectrums of the green and the blue light emitting diodes 12 and 14 is shown. Both emission spectrums extend in a known manner, substantially in the manner of a Gauss curve, whereby the maximum of the emission of the green light emitting diode lies at approximately 505 nanometers and the maximum of the emission of the blue light emitting diode lies at approximately 460 nanometers. The steepness or slope of the flanks of the Gauss curve are such that the emission values of the blue light emitting diode have fallen to substantially zero at the emission maximum of the green light emitting diode, while, conversely, the emission values of the green light emitting diode have fallen to substantially zero at the emission maximum of the blue light emitting diode.

FIG. 2 additionally illustrates the sensitivity of the camphor quinone 20, which is deployed as the photo initiator. The sensitivity spectrum overlaps strongly over the wavelengths with the emission spectrum of the blue light emitting diode.

In accordance with the present invention, an overlapping region 22 exists between the camphor quinone spectrum 20 and the spectrum of the green light emitting diode 12. The overlapping region lies substantially between 460 and 500 nanometers. By actuation of the green light emitting diode 12, the camphor quinone 20 in the dental mass is partially excited so that a pre-hardening of the dental material results.

As is also illustrated in FIG. 2, the maxima of the blue light emitting diode and the camphor quinone 20 do not totally coincide with one another. It is much more the case that the spectral maximum of the blue light emitting diode is generally less than the sensitivity maximum of the camphor quinone, offset toward the short wavelength end by approximately 9 nanometers. The steepness or slope of the emissions curve of the blue light emitting diode is clearly greater than the steepness or slope of the flanks of the spectrum of the sensitivity curve of the camphor quinone, especially in the short wave length region—namely, as shown in FIG. 2, in the left-hand flank.

The diagram in FIG. 2 is normalized so that the maxima of the blue light emitting diode 14, the green light emitting diode 12, and the camphor quinone 20, are plotted to the same height. In this diagram, the spectrums have been chosen such that the spectrum of the camphor quinone 20 surrounds or encompasses the spectrum of the blue light emitting diode 14; that is, the spectrum of the camphor quinone 20 exceeds the maximum of the blue light emitting diode 14 to the left and right thereof by a clearly larger value. These so configured difference surfaces of the spectrum of the camphor quinone are generally the same to the right and left of the maximum of the blue light emitting diode 14, so that the spectrum of the blue light emitting diode, as so regarded, is approximately symmetrically disposed relative to the spectrum of the camphor quinone. It has been demonstrated that by selecting the spectrums to be substantially symmetrical in this manner, a particularly good finishing hardening of the mass can be achieved. If, on the other hand, the maxima of the blue light emitting diode 14 and the camphor quinone 20 are chosen to have the same wavelengths, an asymmetric spectrum results which leads to somewhat less desirable hardening results.

With further regard to the surface, the overlapping region 22 between the green light emitting diode 12 and the camphor quinone 20 comprises approximately one-fourth of the total surface of the spectrum of the camphor quinone. Such a dimensional relationship has shown itself to be particularly favorable for the realization of a partial polymerization.

Figure 3:
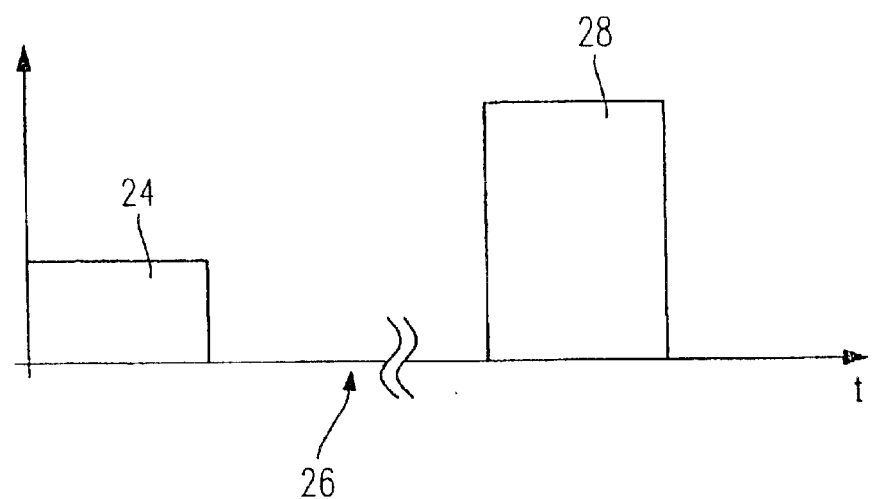
FIG. 3 is a time diagram of the time periods for the hardening operation effected by the light hardening device of the present invention.

The desired hardness also permits itself to be easily adjusted by adjustment of the duration of the light irradiation. As seen in FIG. 3, the green light emitting diode 12 is operated during a first time period 24, with a light emitting intensity of 500 mW/cm². Following the expiration of the first time period 24, the dental mass has been hardened to such an extent that a working or removal of the excess material can be undertaken. This occurs during an excess material removal time period 26, which can be of a duration sufficiently long to permit the dentist to remove the excess material.

The blue light emitting diode is thereafter actuated with a light emitting intensity of 1,000 mW/cm² during a second time period 28.

In the illustrated embodiment of the present invention, the two time periods 24 and 26 have been selected to be of the same duration. It is to be understood, however, that the time periods can be accommodated to the requirements of the situation.

The present invention is, of course, in no way restricted to the specific disclosure of the specification and drawings, but also encompasses any modifications within the scope of the appended claims.

What is claimed is:

1. A light hardening device for hardening a light hardenable mass applied for dental purposes, the light hardenable mass having a photo initiator actuable to initiate hardening of the mass upon irradiation of the photo initiator with light and the photo initiator being sensitive to light across a range of sensitivities which vary from one another at different wavelengths of a set of photo initiator wavelengths, the light hardening device comprising:

a first light emitting diode for emitting light at a range of intensities which vary from one another at different wavelengths of a set of first light emitting diode wavelengths, the range of first light emitting diode intensities overlapping the range of, photo initiator light sensitivities at most only partially; and a second light emitting diode for emitting light at a range of intensities which vary from one another at different wavelengths of a set of second light emitting diode wavelengths, the range of second light emitting diode intensities overlapping the range of photo initiator light sensitivities to a relatively greater extent than the partial overlap of the range of first light emitting diode intensities with the range of photo initiator light sensitivities.

2. A device according to claim 1, wherein the sensitivity maximum of the photo initiator differs from the emission maximum of the second light emitting diode by less than 20 nanometers and, in particular, by less than 15 nanometers, and, preferably, the sensitivity maximum of the photo initiator is at a wavelength which is approximately 10 nanometers larger than the wavelength of the emission maximum of the second light emitting diode.

3. A device according to claim 1, wherein, in a plot of the emissions spectrum of the second light emitting diode and the sensitivity spectrum of the photo initiator in a two dimensional graphical format in which values of the relative intensity or sensitivity are arranged on the Y axis and values of the wavelength are arranged on the X axis, the second light emitting diode has an emission spectrum having a steep flank and, preferably, having two steep flanks, each steep flank having a larger slope than the flanks of the sensitivity spectrum of the photo initiator, and the plot of the emissions spectrum of the second light emitting diode is substantially symmetrically enclosed within the plot of the sensitivity spectrum of the photo initiator.

4. A device according to claim 1, wherein the photo initiator comprises camphor quinone having a sensitivity maximum of approximately 470 nanometers and the emissions maximum of the first light emitting diode has a wavelength larger than 470 nanometers.

5. A device according to claim 1, wherein the emissions value of the first light emitting diode at the wavelength value of the sensitivity maximum of the photo initiator is substantially less than the emissions maximum of the first light emitting diode, and especially, is at least ten times less than the value of the emissions maximum of the first light emitting diode.

6. A device according to claim 1, wherein the light emission intensity of the first light emitting diode as integrated over the surface area of the spectrum of the first light emitting diode is at least 100 mW/cm².

7. A device according to claim 1, wherein the first light emitting diode has its emission maximum in the green spectral region and the maximum is preferably in the region of between 500 to 520 nanometers, and especially, is in the region between approximately 503 to 508 nanometers and, most preferably, is at 505 nanometers.

8. A device according to claim 1, wherein the light emission intensity of the second light emitting diode over the spectrum of the second light emitting diode is at least 300 mW/cm² and, preferably, is between 600 to 1000 mW/cm².

9. A device according to claim 1, wherein the emission maximum of the second light emitting diode is in the region of 440 to 470 nanometers.

10. A device according to claim 1, wherein the first light emitting diode is comprised in a group of first light emitting diodes and the second light emitting diode is comprised in a group of second light emitting diodes, each respective group of the first light emitting diodes and the second light emitting diodes being commonly controllable.

11. A device according to claim 1, and further comprising a control device which is operable to actuate the first light emitting diode before actuation of the second light emitting diode, and the control device actuates the first light emitting diode for a first predetermined time and actuates the second light emitting diode for a second predetermined time.

12. A device according to claim 1, wherein the mass to be applied in the dental application comprises at least two photo initiators.

13. A device according to claim 1, wherein the first light emitting diode has a relatively larger wavelength and a relatively smaller intensity than the second light emitting diode.

14. A method for polymerizing a light hardenable mass applied for dental purposes with a light hardening device, the light hardenable mass having a photo initiator actuable to initiate hardening of the mass upon irradiation of the photo initiator with light and the photo initiator being sensitive to light across a range of sensitivities which vary from one to another at different wavelengths of a set of photo initiator wavelengths, and the light hardening device having two light emitting diodes having differing emission spectrums, the method comprising:

irradiating the mass with a first light emitting diode of the light hardening device during a first time period such that the first light emitting diode emits light in an emission spectrum which at most only partially overlaps the sensitivity spectrum of a photo initiator of the mass.

15. A method according to claim 14, wherein the second light emitting diode of the light hardening device has an emission spectrum which is substantially coincidental with the sensitivity spectrum of a photo initiator of the mass and the method further comprises actuating the second light emitting diode after actuation of the first light emitting diode.

16. A method according to claim 15, wherein the mass is irradiated solely with light emitted by the first light emitting diode during the first time period to at most partially harden the mass, excess mass material is thereafter removed, and, subsequently, the mass is completely hardened by irradiation of the mass by the second light emitting diode.

* * * * *